United States Patent [19]

Heilmann et al.

[11] Patent Number: 4,737,560

[45] Date of Patent: Apr. 12, 1988

[54] POLYMER BEADS

[75] Inventors: Steven M. Heilmann, Afton; Jerald K. Rasmussen, Stillwater; Larry R. Krepski, White Bear Lake; Dean S. Milbrath, Oakdale; Patrick Coleman, Minneapolis, all of Minn.

[73] Assignee: Minnesota Mining and Manufacturing Company, St. Paul, Minn.

[21] Appl. No.: 25,605

[22] Filed: Mar. 13, 1987

[51] Int. Cl.[4] ............................................. C08F 20/58
[52] U.S. Cl. .................................. 526/304; 435/180; 521/38; 526/260
[58] Field of Search .................. 526/260, 304; 521/38; 435/180

[56] References Cited

U.S. PATENT DOCUMENTS

| | | | |
|---|---|---|---|
| 3,511,894 | 5/1970 | Markert | 526/260 |
| 3,583,950 | 6/1971 | Kollinsky | 526/260 |
| 4,070,348 | 1/1978 | Kraemer et al. | 260/79.3 |
| 4,157,418 | 6/1979 | Heilmann | 526/304 |
| 4,224,427 | 9/1980 | Mueller | 526/260 |
| 4,619,867 | 10/1986 | Charbonneau | 526/260 |

OTHER PUBLICATIONS

R. B. Merrifield (*J. Am. Chem. Soc.*, 85, 2149 (1963).
N. K. Mathur, C. K. Narang, and R. E. Wiliams, *Polymers as Aids in Organic Chemistry*, Chapter 2, Academic Press: New York (1980).
L. D. Taylor et al., *Makromol. Chem. Rapid Commun.*, 3, 779 (1982).

*Primary Examiner*—Paul R. Michl

*Attorney, Agent, or Firm*—Donald M. Sell; James A. Smith; Lorraine R. Sherman

[57] ABSTRACT

Azlactone-functional polymer beads are useful reactive supports for the attachment of functional materials to provide novel adduct beads. The adduct beads are useful as complexing agents, catalysts, reagents, and as enzyme or other protein-bearing supports. Novel carboxylate-functional polymer beads, are intermediates in the preparation of the azlactone-functional beads.

Azlactone-functional beads have units of the formula:

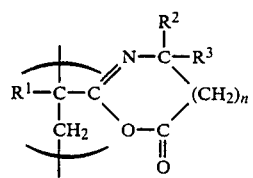

wherein
 $R^1$ is H or $CH_3$,
 $R^2$ and $R^3$ independently can be an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or $R^1$ and $R^3$ taken together with the carbon to which they are joined can form a carbocyclic ring containing 4 to 12 ring atoms, and
 n is an integer 0 or 1.

8 Claims, No Drawings

POLYMER BEADS

FIELD OF THE INVENTION

This invention relates to azlactone-functional polymer beads. In another aspect, carboxylate-functional polymer beads, which are intermediates in the preparation of the azlactone-functional beads, are provided. The azlactone-functional polymer beads are useful reactive supports for the attachment of functional materials to provide novel adduct beads. The adduct beads are useful as complexing agents, catalysts, reagents, and as enzyme or other protein-bearing supports. In additional aspects, methods of preparation of the three types of beads are disclosed.

BACKGROUND OF THE INVENTION

The attachment of useful materials such as catalysts, reagents, chelating or complexing agents, and proteins to insoluble supports is well-known. With the attending advantages of ease of removal and recovery from the system, e.g., by simple filtration, regeneration (if necessary), and recycling coupled with the increased utilization of continuous flow systems in both general chemical processing and diagnostic monitoring procedures, supported materials are ubiquitous in today's technology. One indication of this is the listing of "Polymer-Supported Reagents" as a separate heading in the General Subjects Index of *Chemical Abstracts* beginning in 1982.

Concerning the nature of the insoluble support material, both inorganic polymers (notably silica gel and alumina) and organic polymers have been utilized. Factors, however, such as increased capacity because of better porosity (especially with the so-called "gel-type" polymers which swell somewhat and allow relatively free access by solvent and solute to the bound functionality within the support) and better control of the polar nature of the support (by selection of appropriate comonomers), which has been shown to directly affect reaction rate, have led to a general preference for the organic polymer supports. Polystyrene has been the solid support material most extensively utilized.

The attaching functionality for polystyrene supports most often utilized has been the chloromethylphenyl group. These reactive, solid supports are the so-called "Merrifield resins", so named for R. B. Merrifield (*J. Am. Chem. Soc.*, 85, 2149 (1963)) who received the Nobel Prize in Chemistry in 1984 for these and other achievements. Merrifield resins are extremely useful for conducting solid phase peptide syntheses, but their broad utilization as reactive, solid supports is limited because of the relative nonpolarity of the hydrophobic polystyrene backbone, an oftentimes unpredictable attaching reaction which involves nucleophilic displacement of chloride ion, and a relatively low capacity of reactable chloromethylphenyl groups per gram of polymer. The chloromethylphenyl and other reactive functionalities are discussed by N. K. Mathur, C. K. Narang, and R. E. Williams, "Polymers as Aids in Organic Chemistry", Chapter 2, Academic Press: New York (1980).

The present state of reactive, insoluble supports may be summarized by the statement that no one support is broadly suitable for the many applications of solid-supported materials. The spectrum of properties required varies tremendously depending on the end-use, which includes such diverse applications as mediating organic synthetic transformations, removing precious metals from sea water or heavy metal contaminants from industrial effluents, utilizing supported metals as catalysts for conducting organic reactions and polymerizations, resolving optical isomers, and attaching biomacromolecules.

Azlactones have not been previously utilized as attaching groups on insoluble supports. Azlactones have, however, been proposed to be useful in two instances.

U.S. Pat. No. 4,070,348 teaches the preparation of water-swellable, crosslinked bead copolymers. The copolymers are reactive with proteins primarily by the inclusion of oxirane groups which are the only reactive groups claimed. Several "activated carboxyl groups" (col. 4; line 42), however, are listed including a 2-alkenyl azlactone, 2-isopropenyl-4,4-dimethyl-oxazolone-5 (col. 5; lines 2–3), and reaction of this compound with a primary amino group of a protein is depicted schematically (col. 5; lines 6–14). No additional information or enabling disclosure is given about incorporation of the azlactone into a hydrophilic, crosslinked bead copolymer or reaction of an azlactone-functional insoluble support with a protein or any other functional material. The crosslinked, bead copolymers of U.S. Pat. No. 4,070,348 are all prepared purposely in essentially an anhydrous condition, i.e. with care being taken to exclude water.

L. D. Taylor, et al., *Makromol. Chem., Rapid Commun.*, 3, 779 (1982) have proposed azlactones to be useful as reactive groups on polymeric supports. Only the bulk homopolymerization of 2-vinyl-4,4-dimethylazlactone to form a polymeric "plug" is described. No mention of crosslinking and generation of polymeric beads is given. Furthermore, described at some length is the susceptibility of the poly(azlactone) to hydrolysis, i.e., ring-opening reaction with water [equation (1)]. Hydrolysis is regarded as being very facile, occurring even with traces of moisture often present in organic solvents for the homopolymer, as follows:

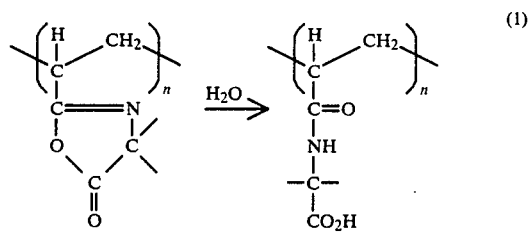

(1)

Based on this account of the propensity toward hydrolysis, it is entirely unexpected that an azlactone-functional support could be selectively reacted with a functional material in aqueous media.

SUMMARY OF THE INVENTION

Briefly, the present invention provides crosslinked, hydrophilic azlactone-functional polymer beads.

In another aspect, the present invention provides crosslinked, hydrophilic carboxylate-functional polymer beads which are intermediates in the preparation of the azlactone-functional polymer beads of the invention. The hydrophilic carboxylate-functional polymer beads have additional utility, for example, as ion exchange resins and as hydrophilic adsorbents.

In a further aspect, the present invention provides novel adduct beads which are produced by a ring opening reaction between the azlactone-functional polymer beads of the invention and functional materials. The adduct beads are useful as complexing agents, catalysts, reagents, and as enzyme- and other protein-bearing supports.

The present invention provides a novel method for the preparation of the three types of beads of the invention. The carboxylate-functional polymer beads are prepared as the polymerization reaction product of:
(i) optionally, at least one free radically addition polymerizable, water soluble monomer,
(ii) at least one water-soluble salt of an N-(meth)acryloylamino acid, and
(iii) at least one crosslinking monomer.

Reaction of a cyclization agent and the carboxylate-functional polymer beads of the invention provides the azlactone-functional polymer beads.

Reaction of the azlactone-functional polymer beads of the invention with functional materials capable of reacting with the azlactone ring (i.e., by a ring-opening reaction) provides the adduct beads of the invention. We have discovered that this adduct-forming reaction occurs to a high degree with a dissolved nucleophile in water solution, especially when the nucleophile is primary amine-functional. This selectivity of reaction is even more surprising when one considers that the concentration of the amine nucleophile is most often substantially lower than that of the water solvent. Before the present invention, it was thought that azlactone groups would predominantly react with water, i.e., hydrolyze, rather than with a dissolved nucleophile.

The hydrophilic or hydrophobic nature of an organic polymer support is extremely important in determining its utility. An obvious advantage of a hydrophilic support is that many of the operations of supported materials are conducted in aqueous media. Water is virtually the exclusive solvent for conducting precious or noxious metal ion removal, diagnostic monitoring of components of biofluids and biosystems, as well as a number of chemical reactions, and it is oftentimes advantageous to utilize a polymer support which will swell in water. The water solvent can facilitate the additional encounter and interaction of a solute and reactive groups within the hydrophilic support as well as at the support-water interface.

Hydrophilic polymer-supported materials find use and are beneficial in non-aqueous systems as well. Functional groups which impart hydrophilicity are highly polar in nature, and supported material functions which are sensitive to solvent effects will be tremendously affected, especially in terms of rate, by the polarity of the polymer backbone. The importance of the polymer backbone in determining the local environment for a supported material has been noted by H. Morawetz, J. Macromol. Sci.—Chem., A-13, 311 (1979) and is herein incorporated by reference.

In this application:
"acryloyl" means not only 1-oxo-2-propenyl but also 1-oxo-2-methyl-2-propenyl resulting from methacryloylation reactions;
"alkyl" means the monovalent residue remaining after removal of a hydrogen atom from a saturated linear or branched chain hydrocarbon having 1 to 14 carbon atoms;
"aryl" means the monovalent residue remaining after removal of one hydrogen atom from an aromatic or heteroaromatic compound which can consist of one ring or two fused or catenated rings having 5 to 12 ring atoms which can include up to 3 heteroatoms selected from S, N, and nonperoxidic O. The carbon atoms can be substituted by up to three halogen atoms, $C_1-C_4$ alkyl, $C_1-C_4$ alkoxy, N,N-di($C_1-C_4$ alkyl)amino, nitro, cyano, and $C_1-C_4$ alkyl carboxylic ester;

"arenyl" means the monovalent residue remaining after removal of a hydrogen atom from the alkyl portion of a hydrocarbon containing both alkyl and aryl groups having 6 to 26 carbon and heteroatoms (wherein the heteroatoms are up to 3 S, N, and nonperoxidic O atoms);

"azlactone" means 2-oxazolin-5-one groups of Formula I and 2-oxazin-6-one groups of Formula II;

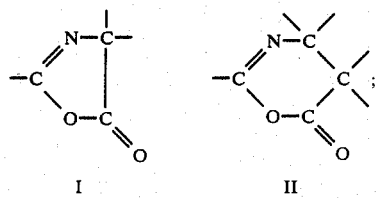

"parts" means parts by weight unless otherwise specified; and
"carboxylate" means

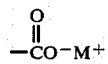

wherein M is hydrogen, ammonium, or an alkali metal such as Li, Na, or K.

Structures and formulae depicted between parentheses are partial structures of crosslinked polymers.

DETAILED DESCRIPTION OF THE INVENTION

The present invention provides azlactone-functional beads having units of the formula:

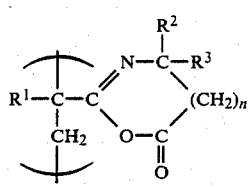

wherein
$R^1$ is H or $CH_3$,
$R^2$ and $R^3$ independently can be an alkyl group having 1 to 14 carbon atoms, a cycloalkyl group having 3 to 14 carbon atoms, an aryl group having 5 to 12 ring atoms, an arenyl group having 6 to 26 carbon and 0 to 3 S, N, and nonperoxidic O heteroatoms, or $R^2$ and $R^3$ taken together with the carbon to which they are joined can form a carbocyclic ring containing 4 to 12 ring atoms, and
n is an integer 0 or 1.

This invention also provides a novel intermediate in the preparation of the azlactone-functional beads of the invention. The novel intermediate is a carboxylate-functional bead having the formula

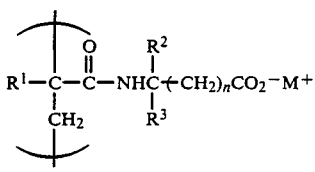

wherein
R¹, R², R³, and n are as previously defined, and
M is a water-solubilizing cation such as hydrogen, ammonium, or an alkali metal such as lithium, sodium, and potassium.

Also provided by this invention are adduct beads having the formula

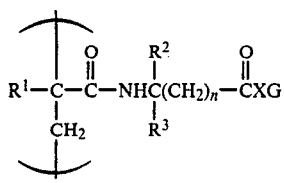

wherein
R¹, R², R³, and n are pr defined, X can be —O—, —S—, —NH, or

wherein R⁴ can be alkyl or aryl, and
G is the residue of HXG which performs the complexing, catalyzing, or reagent function of the adduct beads.

HXG can be a protein (e.g. enzyme), dye, catalyst, reagent, and the like.

The polymer beads of the invention are provided according to the process depicted in FLOW CHART I, below.

FLOW CHART I

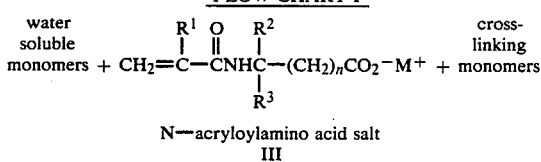

N—acryloylamino acid salt
III

↓ step 1

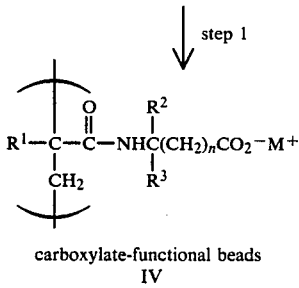

carboxylate-functional beads
IV cyclization agent ↓ step 2

-continued
FLOW CHART I

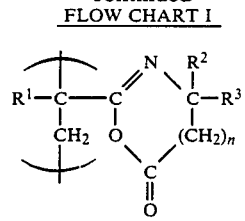

azlactone-functional beads
V functional material HXG ↓ step 3

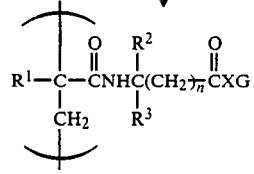

VI
adduct beads

The crosslinked hydrophilic, azlactone-functional polymer beads of Formula V are prepared by a novel two-step process. In the first step the following group of monomers is subjected to a free radical polymerization reaction:

(i) 0 to 98 parts of at least one water soluble monomer;
(ii) 1 to 99 parts of at least one water soluble salt of N-(meth)acryloylamino acid; and
(iii) 1 to 30 parts of at least one crosslinking monomer.

The product of the above polymerization reaction is the crosslinked, hydrophilic, carboxylate-functional beads of Formula IV. The second step of the process involves treating the carboxylate-functional beads with a cyclization agent to form the azlactone-functional beads of the invention.

The degree of hydrophilicity of the polymer support is largely determined by the amount of water soluble monomer employed, although some limited hydrophilicity is imparted by the functional groups created, i.e., amide-amide, amide-ester, or amide-thiolester with amine, alcohol, or thiol nucleophiles (HXG as defined above), by the ring-opening, azlactone/nucleophile reaction (step 3). Therefore, in the strictest sense of the present invention, inclusion of a water soluble monomer is optional. Suitable water soluble monomers exhibit a solubility of at least 3 parts in 100 parts water. Preferred monomers include vinyl group-containing and acryloyl group-containing compounds. A representative list of such monomers includes acrylamide, methacrylamide, N,N-dimethylacrylamide, diacetoneacrylamide, N-vinylpyrrolidone, hydroxyethyl methacrylate, 2-acrylamido-2-methylpropanesulfonic acid and its salts, N-(3-methacrylamidopropyl)-N,N,N-trimethylammonium salts, N,N-dimethylaminoethyl methacrylate, acrylic acid, methacrylic acid, itaconic acid, and combinations thereof. Preferred water soluble monomers are N,N-dimethylacrylamide and N-vinylpyrrolidone.

The N-acryloylamino acid salt monomers include ammonium, sodium, potassium, and lithium salts of N-acryloylamino acids of Formula VII and are prepared by mixing (at <30° C.) equal molar quantities of aqueous solutions of, for example, ammonium hydroxide, sodium hydroxide, potassium hydroxide, or lithium hydroxide and the Formula VII compounds.

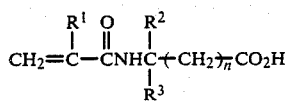

wherein $R^1$, $R^2$, $R^3$, and n are as previously defined.

The N-acryloylamino acid compounds are well-known and can be readily synthesized. For Formula VII compounds in which n=0, either the sodium salt of the appropriate amino acid can be acryloylated, for example, according to K. Huebner, et al., Makromol. Chem., 11, 109 (1970) or, more efficiently, by the method of assignee's co-pending patent application U.S. Ser. No. 865,190 (filed Dec. 23, 1985) which involves the one-pot transformation of a ketone into an N-acryloylamino acid; both procedures are herein incorporated by reference. For Formula VII compounds wherein n=1, a useful preparation is the transformation of 3,3-disubstituted acrylic acids as disclosed by D. I. Hoke, et al., *J. Polym. Sci.: Polym. Chem. Ed.*, 10, 3311 (1972) which is also incorporated by reference.

Insolubilization is a necessary condition for easy removal of the support beads from the system. This is accomplished by inclusion of a monomer which contains a plurality of polymerizable groups and whose participation in a polymerization reaction results in the physical joining of polymer backbones or crosslinking. Crosslinking is also desirable in polymer-supported materials because the mechanical stability is generally substantially enhanced and some degree of control of bead size can be exercized by manipulation of the level of crosslinking, i.e., in general for a given polymerization condition, the greater the amount of crosslinker the smaller the bead size. The degree of crosslinking depends primarily on the intended use of the support material. In all instances the polymers are insoluble in all solvents and possess a molecular weight which is essentially infinite. For applications requiring fairly high capacities and involving relatively small solute reaction partners which can diffuse into the swollen polymer support, low to moderate degrees of crosslinking are desired. According to D.C. Sherrington, *Br. Polym. J.*, 16, 164 (1984), crosslinked swellable supports (referred to as "gel-type" polymers) result from inclusion of from 1 to 20 parts of a difunctional monomer. For applications which allow low capacities, low degrees of physical expansion due to swelling (as in certain operations conducted in confined flow systems such as columns), and which involve large solutes, e.g., biomacromolecules, which cannot because of their large size diffuse into the polymer network, highly crosslinked systems resulting from copolymerization of more than 20 parts of a difunctional monomer are utilized. These are so-called "macroporous" polymers, and solute/support reactions occur primarily at the solvent/support interface.

Suitable crosslinking monomers include α,β-unsaturated esters such as ethylene diacrylate and ethylene dimethacrylate, and α,β-unsaturated amides, such as methylenebis(acrylamide), methylenebis(methacrylamide), N,N'-diacryloyl-1,2-diaminoethane, N,N'-dimethacryloyl-1,2-diaminoethane, and reaction products of 2-alkenyl azlactones and short chain diamines such as those represented by Formulae VIII and IX:

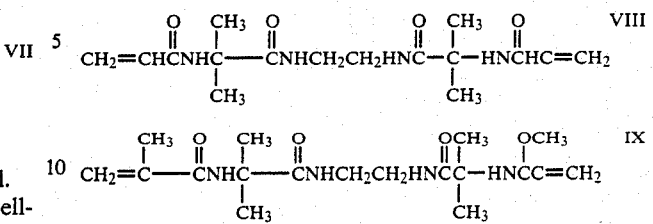

The crosslinking monomers should be at least sparingly soluble in water but need not be as water soluble as defined for the water soluble monomer component. This is not generally a problem for the preparation of gel-type polymers because relatively small proportions of the crosslinking monomers are utilized with relatively large quantities of water solvent, and often the water soluble monomer component, especially N,N-dimethylacrylamide and N-vinylpyrrolidone, will facilitate solution of the crosslinking monomer. For macroporous polymers, however, in which the concentration is >20 parts it may be necessary to add a co-solvent which will facilitate dissolution of the crosslinking monomer. Suitable co-solvents include N,N-dimethylformamide, N,N-dimethylacetamide, N-methylpyrrolidone, and dimethylsulfoxide.

The technique of polymerization employed in the present invention is often referred to as "reverse-phase" or "inverse" suspension polymerization, and a general discussion of this technique by M. Munzer, et al., "Suspension Polymerizations from Non-Aqueous Media", in "Polymerization Processes" edited by C. E. Schildknecht and I. Skeist, Wiley-Interscience: New York, pp. 123–124 (1977) is herein incorporated by reference. The reversal of the normal suspension polymerization technique (in which water is the usual suspending medium) is necessary because the monomers of the present invention are soluble in water and therefore require a water immiscible suspending medium.

The primary purpose of the suspending medium, besides functioning as an inert medium for dispersion of the polymerizable phase, is to dissipate the heat generated in the polymerization reaction. An important characteristic of the suspending medium is its density. In order to obtain spherical polymer beads of uniform size, the beads, once formed, should not exhibit a tendency to sink or float in the suspending medium. Therefore, the suspending medium and aqueous phases should be of approximately the same density.

The actual polymerization occurs in individual droplets of water containing the dissolved monomers and initiator. The droplets are formed and maintained in the suspending medium by vigorous agitation, and their size is controlled by the addition of various suspending agents which are surface active molecules that generally contain both hydrophobic and hydrophilic parts.

In and of itself, the polymerization step is not a novel aspect of the present invention. As is apparent to one skilled in the art, the nature of the suspending medium, the amount of water employed, the initiation system, the amount of crosslinking agent, the stirring rate, and the suspending agent are all essentially independent and important variables that determine the shape and size of the polymeric beads. While not wishing to be bound by any particular set of polymerization conditions, we have found the reverse-phase suspension polymerization procedure described by G. L. Stahl, et al., *J. Org. Chem,* 44, 3424 (1979) to be exceedingly useful. In that procedure a mixture of heptane and carbon tetrachloride is utilized as the suspending medium; the initiation system is the ammonium persulfate/N,N,N',N'-tetramethyl-1,2-diaminoethane redox couple; the stirring rate is 300 rpm; and the suspending agent is sorbitan sesquioleate. Substitution of the various components by comparable materials can certainly be made, and such substitutions would not be outside the spirit and scope of the present invention.

Step two of the process of the invention consists of conversion of the carboxylate-functional beads into azlactone-functional beads. This is accomplished using a cyclization agent. A cyclization agent is a reagent that can react with the carboxylate-functional beads to form an intermediate adduct which is susceptible to intramolecular attack by the amide carbonyl group to form azlactone groups according to Flow Chart II. This susceptibility is chiefly accomplished by forming a good leaving group (⊖O(CA) below) for the nucleophilic attack by the carbonyl.

FLOW CHART II

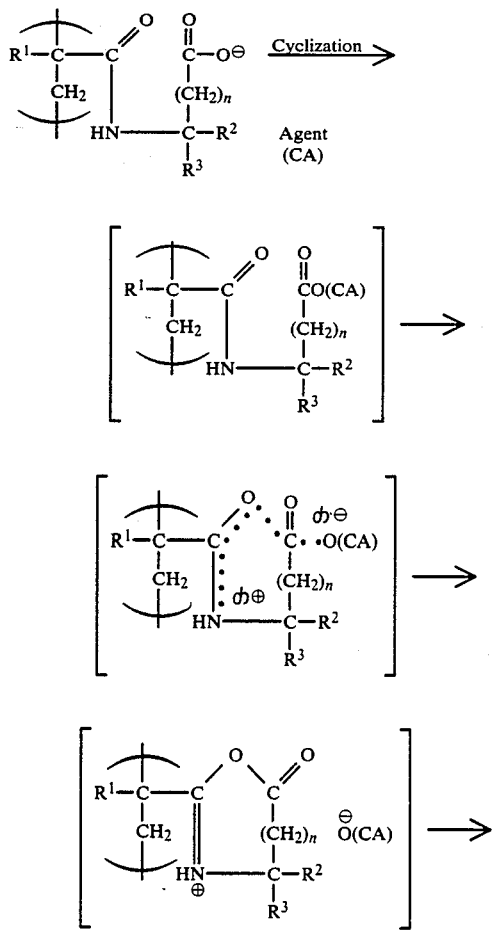

-continued
FLOW CHART II

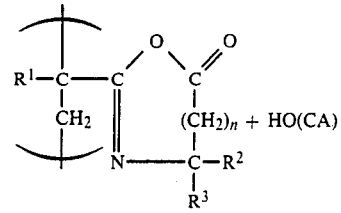

wherein $R^1$, $R^2$, $R^3$, and n are as defined above.

(Structures and formulae depicted between parentheses are partial structures of crosslinked polymers depicting side chains that actively participate in the cyclization reaction. Use of brackets has the usual meaning of chemical intermediates or activated complexes. Dotted lines mean partial bonds, and α means partial ionic charges.)

Useful cyclization agents for transformation of the carboxylate-functional beads include, by way of example, acetic anhydride, trifluoroacetic anhydride, and alkyl chloroformates such as methyl, ethyl, and isopropyl chloroformates. Carbodiimides such as N,N'-dicyclohexylcarbodiimide can be effectively utilized but require an additional step of acidifying the carboxylate-functional beads to form carboxyl-functional beads which can then be cyclized to azlactone-functional beads using the carbodiimide reagent. To facilitate understanding of the cyclization step of the invention, the intermediates that would result by employing the aforementioned cyclization agents are depicted below in order of mention.

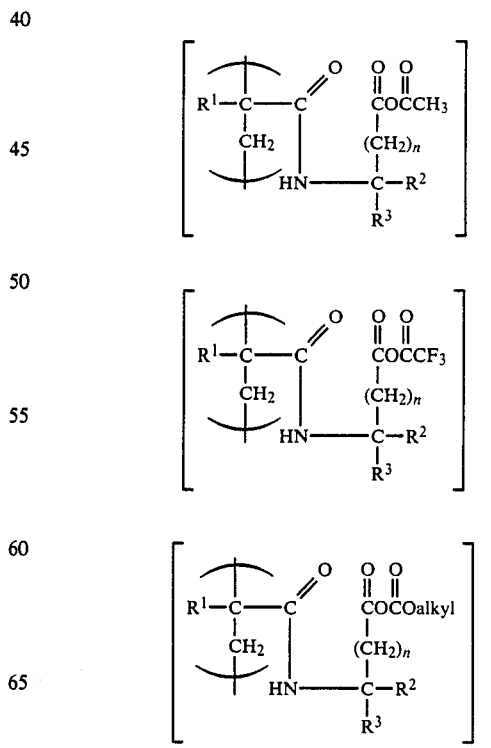

-continued

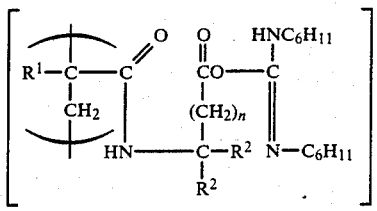

The progress of the cyclization reaction can be easily monitored by examination of the infrared spectrum of the polymer beads. Appearance of a carbonyl stretching absorption at about 1820 cm$^{-1}$ is evidence of azlactone groups. Indeed, one reason azlactone groups are so useful as linkages for covalent attachment to polymers is the ability to monitor reactions by observation of this infrared absorption, either the appearance of it in the synthesis of the azlactone-functional beads or the disappearance of it in the subsequent reaction with a functional material. This absorption is strong, very characteristic of azlactones, and located in a region of the infrared spectrum where essentially no other common absorptions are observed. This is a decided advantage over other linking functional groups such as the chloromethylphenyl and oxirane which lack these unique features in their infrared spectra. A convenient analytical method for monitoring attaching reactions really does not exist with these latter groups.

Because of its low cost and availability, acetic anhydride is a preferred cyclization agent. Typically, the carboxylate-functional beads are covered with acetic anhydride, and the mixture is warmed at temperatures from 40°-100° C., preferably 80°-100° C., for a period of 2-24 hours. After the cyclization reaction, the polymer beads are filtered. What also makes acetic anhydride particularly preferred is that the by-product of cyclization, the alkali metal acetate salt, is fairly soluble in acetic anhydride and can easily be removed from the azlactone-functional beads. The beads can then be dried directly or, as is often conducted, subjected to a series of washing operations with non-reactive organic solvents such as acetone, toluene, ethyl acetate, heptane, and chloroform prior to drying.

The crosslinked, hydrophilic, azlactone-functional polymer beads of the invention have now been formed and are ready for reaction with a functional material. As indicated earlier, a surprising discovery was that functional materials can often be attached to azlactone-functional beads of the invention in solvents such as water that have heretofore been thought of as being reactive with azlactones. "Material" as used herein means the principal chemical entity that is desired to be attached to a polymer support to accomplish a specific purpose. Stated another way, "material" means that portion or residue of the "functional material" which actually performs the complexing, catalytic, or reagent end-use. "Functional" for purposes of this invention means that portion of the "functional material" which contains a group that can react with an azlactone. "Functional" groups useful in the present invention are hydroxy, primary amine, secondary amine, and thiol. These groups react, either in the presence or absence of suitable catalysts, with azlactones by nucleophilic addition as depicted in equation (2) below.

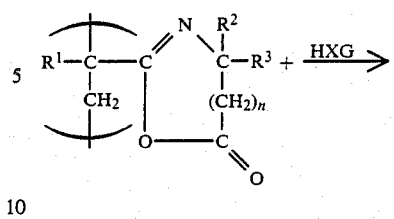

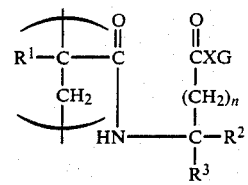

wherein $R^1$, $R^2$, $R^3$, n, X, and G are as previously defined.

Depending on the functional group present in the functional material, catalysts may be required to achieve effective attaching reaction rates. Primary amine functional groups require no catalysts. Acid catalysts such as trifluoroacetic acid, ethanesulfonic acid, toluenesulfonic acid, and the like are effective with hydroxy and secondary amine functional groups. Amine bases such as triethylamine, 1,8-diazabicyclo[5.4.0]undec-7-ene (DBU), and 1,5-diazabicyclo[4.3.0]non-5-ene (DBN) are effective as well for hydroxy and thiol functional groups. The level of catalyst employed is generally from 1 to 10 parts, preferably 1 to 5 parts.

As is apparent to one skilled in the art, specific reaction conditions such as solvent, temperature, level of catalyst, etc. vary tremendously depending on the functional material that is to be attached. Because of the myriad of functional materials that have been or could be attached to polymer supports, any listing of functional materials beyond the generic HXG of equation (2) and FLOW CHART I would be incomplete and somewhat unnecessary, as the inventive aspects of the present invention do not reside with the functional materials.

Having described the invention in general terms, objects and advantages of the invention are more specifically illustrated by the following examples. The particular materials and amounts thereof recited in the examples, as well as other conditions and details, should not be construed to unduly limit this invention.

EXAMPLE 1

This example teaches the preparation of a gel-type polymer of the invention.

Preparation of Copoly(N,N-Dimethylacrylamide: 2-Vinyl-4,4-Dimethylazlactone:Methylene-bisacrylamide) (46:46:8)

Step 1: Preparation of Copoly(N,N-Dimethylacrylamide (DMA): N-Acryloylmethylalanine Sodium Salt (NaAMA):Methylenebisacrylamide (MBA)) (44.6:50.4:7.8): A two-liter creased, round bottomed flask equipped with a mechanical stirrer (stirring rate ca. 300 rpm), nitrogen inlet, thermometer, and condenser was charged with heptane (1043 mL) and carbon tetrachloride (565 mL). This solution was stirred and sparged with nitrogen for 15 minutes. A separate solution was prepared consisting of a sodium hydroxide solution (6.6 grams; 0.165 mole dissolved in 85 mL of water), N-acryloylmethylalanine (AMA) (25.98 grams; 0.165 mole), DMA (23 grams; 0.232 mole), MBA (4 grams; 0.026 mole), and ammonium persulfate (1 gram; 0.004 mole) and added to the organic suspending medium. Sorbitan sesquioleate (Arlacel TM 83, ICI Americas, Inc., Wilmington, Del.) (2 mL) was added and the mixture stirred and sparged with nitrogen for 15 minutes. N,N,N',N'-tetramethyl-1,2-diaminoethane (2 mL) was added and the reaction temperature rose fairly quickly from 21° C. to 33° C. The mixture was stirred at room temperature for three hours. The mixture was efficiently filtered using a "D" (>21 microns) sintered glass funnel, and the filter cake washed thoroughly and repeatedly with acetone. After drying at 60° C. and <1 Torr. for 12 hours, the dry solid (52 grams) was sieved and separated into four fractions: beads <38 microns, 12.32 grams; beads between 38 and 63 microns, 19.83 grams; beads between 63 and 90 microns, 4.56 grams; and beads >90 microns, 13.95 grams. Employing an optical microscope arrangement consisting of a Nikon Nomarski Differential Interference Contrast Microscope, a Dage Newvicon video camera, a Sony ¾" video recorder, and a Perceptive Systems, Inc. digital image processor with accompanying software, it was determined that the 38–63 micron sample consisted of quite spherical beads (average aspect ratio=0.87) which swell in water with an accompanying increase in volume of from 35–50%.

Step 2: Cyclization to Copoly(DMA:2-vinyl-4,4-dimethylazlactone (VDM):MBA) (46:46:8): Acetic anhydride (100 mL) was added to 15.1 grams of the 38–63 micron beads prepared in Step 1. The mixture was heated to 100° C. for two hours. After cooling and filtering, the beads were placed in a Soxhlet extraction apparatus and were extracted with ethyl acetate for 16 hours. After drying at 60° C. and <1 Torr., the beads weighed 12.6 grams. Infrared analysis (Nujol mull) showed a strong azlactone carbonyl absorption at about 1820 cm$^{-1}$.

EXAMPLE 2

This example teaches use of the reaction product of 1,2-diaminoethane and VDM as a crosslinking monomer.

Preparation of N,N'-bis(2-acrylamido-2-methylpropionyl)-1,2-diaminoethane

A 100 mL, three-necked, round bottomed flask equipped with a magnetic stirring bar, a dropping funnel, thermometer, and condenser was charged with VDM (13.9 grams; 0.10 mole) and tetrahydrofuran (50 mL). A solution of 1,2-diaminoethane (3.0 grams; 0.05 mole) in tetrahydrofuran (10 mL) was added dropwise such that the temperature did not exceed 30° C. After stirring overnight the reaction mixture was filtered to remove a white solid which after washing with hexane and drying at <1 Torr. weighed 15.8 grams (93% yield). The solid melted at 207°–210° C. and exhibited satisfactory elemental analyses and spectral characteristics for the desired material, which is the compound of Formula VIII in the specification.

Preparation of Copoly(N,N-Dimethylacrylamide:2-Vinyl-4,4-Dimethylazlactone:N,N'-Bis(2-Acrylamido-2-MethylPropionyl)-1,2-Diaminoethane) (55:42.7:2.3)

The two-step procedure of EXAMPLE 1 was utilized except MBA was replaced by the above prepared crosslinking monomer (1.0 gram; 0.003 mole). A sample (15.1 grams) of the intermediate carboxylate-functional polymer was treated with acetic anhydride to yield, after washing and drying, 11.0 grams of the azlactone-functional polymer.

EXAMPLE 3

This example teaches the reaction of a gel-type polymer and a relatively low molecular weight, intrapolymer support-diffusible functional material. The example further teaches a procedure for quantitative determination of azlactone groups.

The procedure is a variation of a quantitative analysis of isocyanates and isothiocyanates using n-butylamine (cf. S. Siggia, "Quantitative Organic Analysis via Functional Groups", John Wiley & Sons: New York, p. 558 (1963)). Generally, the procedure involves treatment of the azlactone-functional beads with standard triethylamine in N,N-dimethylformamide (DMF) to react with and determine the concentration of any uncyclized carboxyl groups. To another sample of beads, excess standard n-butylamine in DMF is added and shaken for 24 hours at room temperature. The excess concentration of n-butylamine is then determined by potentiometric titration with standard acid as an indirect measure of the concentration of azlactone groups. Using this method with the beads of EXAMPLE 2, three separate determinations showed minimal, i.e., <0.3 milliequivalents/gram of resin, carboxyl content and an average azlactone content of 2.2 meq/g. Theoretical azlactone content was 3.1 meq/g. Therefore, over 70% of the theoretical azlactone groups had formed and were accessible by the n-butylamine functional material!

EXAMPLE 4

This example further teaches the reaction of a gel-type polymer with a relatively small functional material, N-(3-aminopropyl)morpholine, but in an aqueous reaction solvent. Determination of reactable azlactone content is made by measuring the increase in % nitrogen of the reacted beads. This procedure is more time consuming than the quantitative analysis method outlined in EXAMPLE 3, but comparison of the results serves as a check on the accuracy of the titration method.

A gel-type polymer consisting of DMA:VDM:MBA (53.8:41.7:4.5) was prepared as in EXAMPLE 1; the theoretical % nitrogen present in the beads should be 12.6%; experimentally observed using a Kjeldahl method was 12.1%.

The azlactone-functional beads (1.44 grams; containing approximately 0.004 mole of azlactone groups), N-(3-aminopropyl)-morpholine (0.80 gram; 0.0055 mole), and 15 mL of a standard aqueous pH 9 buffer solution were placed in a 100 mL, round bottomed flask and stirred at room temperature. After four hours the beads were filtered, washed repeatedly with deionized water, and dried at 60° C. and <1 Torr. The resulting adduct possessed a nitrogen content of 13.8%. Theoretically, the increase in nitrogen should have been 17.4%. The experimentally observed increase of 12.3% again indicates that 70% of the azlactone groups had formed and reacted. This result is in excellent agreement with the titration procedure result of EXAMPLE 3. Furthermore, the result indicates that measurable hydrolysis in the aqueous pH 9 buffer solution did not occur and that virtually quantitative attaching reactions can take place in aqueous media at an elevated pH.

EXAMPLES 5-7

These examples illustrate how polymer bead size can be controlled by the level of crosslinking monomer.

The procedure of Step 1 of EXAMPLE 1 was utilized to prepare the carboxylate-functional beads of the following examples. Average particle diameters were determined using an optical microscope equipped with a Zeiss IBAS ™ Image Analyzer. It is apparent that as the level of crosslinker increases the particle diameter decreases.

| EX-AMPLE | Monomer wts. (g) DMA | NaAMA | MBA | Wt % cross-linker | Average particle Diameter (micrometers) |
|---|---|---|---|---|---|
| 5 | 24 | 24 | 2 | 4 | 67.5 |
| 6 | 23 | 23 | 4 | 8 | 42.2 |
| 7 | 21 | 21 | 8 | 16 | 32.4 |

EXAMPLES 8-10

These examples teach the preparation of macroporous polymers of the invention. They furthermore teach utilization of a co-solvent to facilitate dissolution of the crosslinking monomer.

The method of EXAMPLE 1 was utilized except the monomers and initiator were dissolved in water (75 grams) and DMF (30 grams). The azlactone content was determined utilizing the titration procedure of EXAMPLE 3.

| EXAMPLE | Step 1 changes DMA | NaAMA | MBA | Average particle diameter (micrometers) | Step 2 beads azlactone content theoretical | (meq/g) Measured |
|---|---|---|---|---|---|---|
| 8 | 34.02 | 4.48 | 12.5 | 26.0 | 0.5 | 0.29 |
| 9 | 30.55 | 8.95 | 12.5 | 20.5 | 1.0 | 0.52 |
| 10 | 27.08 | 13.42 | 12.5 | 25.0 | 1.5 | 1.10 |

EXAMPLE 11

This example teaches the preparation of a macroporous polymer with N-methacryloylmethylalanine sodium salt (NaMMA) instead of NaAMA. The resulting azlactone-functional bead of Formula V was formed with $R^1=CH_3$.

The procedure of EXAMPLE 9 was utilized except that NaMMA (9.65 grams) was substituted for the NaAMA. The resulting azlactone-functional beads which were formed after treatment with acetic anhydride had an average particle diameter of 22.4 micrometers and an azlactone functionality of 0.68 meq/gram.

EXAMPLE 12

This example teaches the preparation of a macroporous polymer with N-vinylpyrrolidone as the water soluble monomer component. The procedure and monomer charges of EXAMPLE 9 were utilized except the DMA was replaced by N-vinylpyrrolidone. The average particle diameter of the beads resulting from Step 1 was 19.3 micrometers. Cyclization afforded azlactone-functional beads which possessed a strong azlactone carbonyl absorption band at about 1820 $cm^{-1}$ in the infrared.

EXAMPLE 13

This example teaches the synthesis of a six-membered ring azlactone (2-oxazin-6-one) functional polymer bead. The procedure of EXAMPLE 9 was utilized except 3-acrylamido-3-methylbutyric acid sodium salt (9.65 grams) was utilized instead of NaAMA. After cyclization the 2-oxazin-6-one functional beads possessed an average diameter of 28.5 micrometers and a functional level of 0.16 meq/g.

EXAMPLE 14

This example teaches the reaction of an azlactone-functional polymer bead with a protein functional material. Protein A (from *Staphylococcus aureus*) is a commercially available material (Pharmacia Fine Chemicals; Division of Pharmacia, Inc., Piscataway N.J.). The protein, as well as the protein immobilized on a Sepharose ™ support, has manifold uses. Pharmacia Fine Chemicals has issued two publications: "Protein A (*S. aureus*): Selected Applications of Free and Labeled Protein A", revised edition (January 1982) and "Protein A-Separose CL-4B: Selected Applications References", revised edition (January 1982); both publications are herein incorporated by reference.

Preparation of Radio-labeled Protein A

Protein A (2.5 mg) (Genzyme Corp., Boston, Mass.) was dissolved in 10 mM potassium phosphate buffer (pH 7.0; 0.6 mL) and two Iodo-beads (an insoluble form of chloramine T; Pierce Chemical Co., Rockford, Ill.) were added to catalyze the addition of iodine to tyrosine residues. The reaction was initiated by the addition of 1.5 mCi of NaI (carrier-free $^{125}I$, New England Nuclear Co., N. Billerica, Mass.). The reaction was incubated at 20° C. for 30 minutes with vigorous manual shaking at five minute intervals. Protein A (both iodinated and unmodified forms) was separated from NaI by elution through a Pharmacia PD-10 size exclusion column in the same phosphate buffer. The fractions which contained protein were combined, aliquotted, and frozen at −15° C. until used. Specific radioactivity on day 0 was 154,000 cpm/ug. All subsequent calculations were corrected for the radioactive half-life of $^{125}I$ of 60 days. Radioactive Protein A was not used beyond six weeks after iodination.

Reaction of the Radio-labeled Protein A with an Azlactone-Functional Bead

The azlactone-functional polymer utilized was that prepared in EXAMPLE 5. The polymer beads (0.010 gram) were placed in a centrifuge tube and were covered with a solution consisting of the labeled Protein A preparation above (100 ul) and 400 ul of a phosphate buffer solution (pH 7.5). The mixture was shaken gently at room temperature for 90 minutes. The tube was centrifuged, and the original supernatant and five successive washes (1 ml of pH 7.5 buffer) were collected and their $^{125}$I content determined using a Packard Auto-Gamma Scintillation Spectrometer Model 5230. The original supernatant exhibited 42,415 cpm (above background); first wash: 6722; second wash: 836; third wash: 202; fourth wash: 48; and fifth wash: 18 cpm. Ethanolamine (400 microliters of 0.5 M in pH 7.5 phosphate buffer) was added and shaken with the beads for 90 minutes to react with all the remaining azlactone residues. Finally, after an additional four washes with buffer solution the beads and the reaction vessel were counted and exhibited 7002 and 1865 cpm, respectively. This correlates to a level of 2.54 micrograms of Protein A/10 mg of beads.

A CONTROL was conducted in the same manner except the order of addition of Protein A and ethanolamine was reversed. The CONTROL exhibited a level of 0.14 microgram of Protein A/10 mg of beads.

In a similar fashion, the effects of the catalyst DBU were examined, with the DBU (25 microliters) being added to the initial Protein A buffer solution. The result was a level of 3.90 micrograms of Protein A/10 mg of beads.

EXAMPLE 15

This example illustrates that the Protein A is not just adsorbed or adhering to the beads in some fashion but is actually covalently bound to the polymer beads. The amount of covalently bound protein may be estimated by determining the amount of protein resistant to sodium dodecylsulfate (SDS) treatment. SDS denatures protein so that only those molecules which are covalently bound will remain attached to the beads.

In this experiment, the polymer beads of EXAMPLE 14 (having 3.90 micrograms Protein A/10 mg of beads) (0.010 gram) were incubated with 1% SDS (500 microliters) at 37° C. for two hours, followed by centrifugation, and five buffer (550 microliters; pH 9.5) washes. Analysis of the radioactivity of the beads revealed that 73% of the protein remained attached to the beads.

EXAMPLE 16

This example illustrates that the Protein A attached to the polymer beads remains active to accomplish a specific function and is not denatured in the attaching process.

Biologically active Protein A can be assayed by determining the amount of antibody which it can bind. Antibody (IgG) conjugated with an enzyme marker, alkaline phosphatase was purchased from Cooper Biomedical (Malvern, Pa.).

In this experiment, 1.0 mg of the polymer beads of EXAMPLE 5 were reacted with unlabeled Protein A and ethanolamine as described in EXAMPLE 14. After the washing steps, Protein A and CONTROL beads were resuspended in the alkaline phosphatase assay solution (0.1 M sodium glycinate, 1.0 mM $ZnCl_2$, 1.0 mM $CaCl_2$, 6.0 mM p-nitrophenyl phosphate, pH 10.4) and rocked continuously to promote mixing. Every 10 min. the absorbance of the supernatant solution was determined at 405 nm. The absorbance increased linearly at 5 to 15 times the CONTROL rate, depending on the amount of immobilized Protein A. This showed that the protein remained active.

EXAMPLE 17

This example teaches that the attaching reaction with a protein in aqueous media is rapid.

The beads of Example 6 were reacted with radiolabeled Protein A as described in Example 14 except that the quenching and washing steps were initiated at various times from 5-180 min. The "zero time" was prepared by addition of the quencher ethanolamine first. The reaction was performed in pH 8.5 sodium pyrophosphate buffer with DBU. It was observed that at 5 minutes 1.34 micrograms of Protein A/10 mg of beads were bound. This was 80% by weight of the amount bound at 180 minutes.

Various modifications and alterations of this invention will become apparent to those skilled in the art without departing from the scope and spirit of this invention, and it should be understood that this invention is not to be unduly limited to the illustrative embodiments set forth herein.

We claim:

1. A carboxylate-functional polymeric bead which is the aqueous phase reaction product of:
   (i) 0 to 98 parts of free radically addition polymerizable, water soluble monomers,
   (ii) 1 to 99 parts of a water soluble salt of N-(meth)acryloylamino acid, and
   (iii) 1 to 30 parts of at least one crosslinking monomer.

2. A carboxylate-functional bead according to claim 1 having units of the formula:

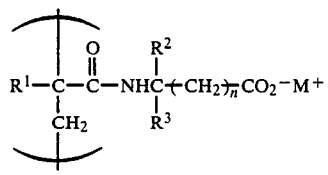

wherein
$R^1$, $R^2$, $R^3$ and n are as previously defined, and
M is a water-solubilizing cation, and
n=0 or 1.

3. The carboxylate-functional bead according to claim 2 wherein $R^1$, $R^2$, and $R^3$ are methyl and n=0.

4. A method comprising the steps of:
   (a) polymerizing together
      (i) 0 to 98 parts of at least one free radically addition polymerizable, water soluble monomer,
      (ii) 1 to 99 parts of at least one water soluble salt of N-(meth)acryloylamino acid, and
      (iii) 1 to 30 parts of at least one crosslinking monomer,
   (b) isolating the resulting carboxylate-functional polymer beads.

5. The method according to claim 4 further comprising the steps of:
   (c) reacting said carboxylate-functional beads with a cyclizing agent, and
   (d) isolating the resulting azlactone-functional polymer beads.

6. The method according to claim 5 further comprising the steps of:
   (e) reacting the azlactone-functional polymer beads with a functional material capable of reacting with said azlactone in a ring-opening reaction, and
   (f) isolating the resulting adduct beads.

7. The method according to claim 6 wherein said step (e) takes place in aqueous solution.

8. The method according to claim 6 wherein said functional material is selected from the group consisting of proteins, catalysts, reagents, and dyes.

* * * * *

UNITED STATES PATENT AND TRADEMARK OFFICE
CERTIFICATE OF CORRECTION

PATENT NO. : 4,737,560

DATED : April 12, 1988

INVENTOR(S) : Steven M. Heilmann et al.

It is certified that error appears in the above-identified patent and that said Letters Patent is hereby corrected as shown below:

Col. 18, line 37, delete "$R^1$, $R^2$, and $R^3$ and n are as previously defined" and insert therefor -- $R^1$ is H or $CH_3$, $R^2$ and $R^3$ independently can be an alkyl group having 1 to 14 carbon atoms, a cycloalkyl group having 3 to 14 carbon atoms, an aryl group having 5 to 12 ring atoms, an arenyl group having 6 to 26 carbon and unitary heteroatoms, or $R^2$ and $R^3$ taken together with the carbon to which they are joined can form a carbocyclic ring containing 4 to 12 ring atoms --

Signed and Sealed this

Nineteenth Day of September, 1989

Attest:

DONALD J. QUIGG

Attesting Officer

Commissioner of Patents and Trademarks